(12) United States Patent
Quaedflieg et al.

(10) Patent No.: US 7,361,775 B2
(45) Date of Patent: Apr. 22, 2008

(54) PROCESS FOR THE PREPARATION OF (S)-GLYCERALDEHYDE ACETONIDE

(75) Inventors: Peter Jan Leonard Mario Quaedflieg, Waalre (NL); Franciscus Alphons Marie Lommen, Horst (NL); Robert Jan Vijn, Venlo (NL); Danniël Adrianus Franciscus Jacobus Boxtel Van, Weert (NL)

(73) Assignee: DSM IP Assets B.V., Heerlen (NL)

( * ) Notice: Subject to any disclaimer, the term of this patent is extended or adjusted under 35 U.S.C. 154(b) by 36 days.

(21) Appl. No.: 10/574,693

(22) PCT Filed: Oct. 7, 2004

(86) PCT No.: PCT/EP2004/011343

§ 371 (c)(1),
(2), (4) Date: Jul. 6, 2006

(87) PCT Pub. No.: WO2005/037819

PCT Pub. Date: Apr. 28, 2005

(65) Prior Publication Data
US 2007/0073068 A1    Mar. 29, 2007

(30) Foreign Application Priority Data
Oct. 7, 2004   (EP)  ................... 03078130

(51) Int. Cl.
*C07D 317/26*    (2006.01)

(52) U.S. Cl. ..................................... 549/464
(58) Field of Classification Search ................. 549/464
See application file for complete search history.

(56) References Cited

FOREIGN PATENT DOCUMENTS

| EP | 0 143 973 | 6/1985 |
|----|-----------|--------|
| EP | 143973 | * 6/1998 |

* cited by examiner

*Primary Examiner*—D. Margaret Seaman
*Assistant Examiner*—Nizal S. Chandrakumar
(74) *Attorney, Agent, or Firm*—Nixon & Vanderhye P.C.

(57) ABSTRACT

The invention relates to a process for the preparation of (S)-glyceraldehyde acetonide in aqueous solution from 3,4-O-isopropylidene-L-threonic acid or a salt thereof in aqueous solution, and hypochlorite in aqueous solution wherein the aqueous hypochlorite solution has a pH>7.5 and wherein during addition of at least 0.1 molar equivalents of hypochlorite based on the amount of 3,4-O-isopropylidene-L-threonic acid, an acid solution is not simultaneously added. The invention also relates to a process according to the invention, wherein 3,4-O-isopropylidene-L-threonic acid or a salt thereof is prepared from 5,6-O-isopropylidene-L-ascorbic acid or a salt thereof in the presence of $H_2O_2$ and a base in a manner known per se, wherein excess $H_2O_2$ is optionally removed by catalase. The invention also relates to a process according to the invention, wherein 5,6-O-isopropylidene-L-ascorbic acid or a salt thereof is prepared by reacting L-ascorbic acid or a salt thereof with an acetonide forming agent, preferably in the presence of an acid catalyst.

12 Claims, No Drawings

PROCESS FOR THE PREPARATION OF (S)-GLYCERALDEHYDE ACETONIDE

This application is the US national phase of international application PCT/EP2004/011343 filed 7 Oct. 2004 which designated the U.S. and claims benefit of EP 03078130.6, dated 7 Oct. 2003, the entire content of which is hereby incorporated by reference.

The invention relates to a process for the preparation of (S)-glyceraldehyde acetonide from 3,4-O-isopropylidene-L-threonic acid or a salt thereof in aqueous solution and hypochlorite in aqueous solution.

(S)-glyceraldehyde acetonide is a useful intermediate in the synthesis of, for instance drugs, agricultural chemicals etc.

A process for the preparation of (S)-glyceraldehyde acetonide is known from EP-A-0 143 973, wherein (S)-glyceraldehyde acetonide is prepared from 3,4-O-isopropylidene-L-threonic acid or a salt thereof and hypochlorite under acidic conditions. To obtain and maintain the acid conditions, according to EP-A0 143 973 an aqueous mineral acid solution and an aqueous hypochlorite solution are separately but simultaneously added to an aqueous solution of 3,4-O-isopropylidene-L-threonic acid or a salt thereof or alternatively, an acidified solution of hypochlorite ion or hypochlorous acid prepared beforehand is added.

A major disadvantage of the separate but simultaneous addition of the two solutions (the acid and the alkaline hypochlorite) is that, especially on a large scale, it is very difficult to control the reaction engineering-wise, for example with respect to the pH. A major disadvantage of the addition of an acid solution of hypochlorite ion or hypochlorous acid is that such a solution is highly unstable and can easily lead to the liberation of $Cl_2$-gas causing hazardous situations.

Therefore, it is the object of the invention to provide a process for the preparation of (S)-glyceraldehyde acetonide, wherein the disadvantages of the prior art are overcome.

This object is achieved by using an aqueous solution of hypochlorite with a pH>7.5 and by not adding an acid solution simultaneously during addition of at least 0.1 molar equivalents of the hypochlorite based on the amount of 3,4-O-isopropylidene-L-threonic acid or a salt thereof.

Additionally, with the process of the invention, it has surprisingly been found that a higher yield of (S)-glyceraldehyde acetonide based on 3,4-O-isopropylidene-L-threonic acid or a salt thereof is obtained and also that less by-products are formed than with the process as described in EP-A-0 143 973. The yield of (S)-glyceraldehyde acetonide obtained with the process described in example 7 of EP-A-0 143 973 was shown to be unacceptably low (only 49%).

The hypochlorite may be added in the form of an aqueous solution of a hypochlorite salt, for example an alkali metal hypochlorite salt, for example sodium hypochlorite that is commercially available or an earth alkali metal hypochlorite salt, for example calcium hypochlorite that is commercially available.

Preferably, the aqueous hypochlorite solution used in the process of the invention has a pH>8.0, more preferably a pH>9.0, in particular a pH>10.0 is. Commercially available hypochlorite solutions usually have a pH well above 7.5. In case the hypochlorite solution does not have the desired pH, the person skilled in the art knows how to increase the pH of the solution (for example by adding a strong base, for example sodium hydroxide). Preferably the pH of the hypochlorite solution is <14, more preferably <13.

Preferably, an acid solution is not simultaneously added during addition of at least 0.3, more preferably at least 0.5, in particular at least 0.8, more in particular at least 1.0, even more in particular at least 1.2, even more in particular 1.5 molar equivalents of hypochlorite based on the amount of the threonic acid part of 3,4-O-isopropylidene-L-threonic acid or a salt thereof. Most in particular an acid solution is not simultaneously added during the addition of between 1 and 3 molar equivalents of hypochlorite based on the amount of 3,4-O-isopropylidene-L-threonic acid or a salt thereof. According to a particularly preferred embodiment of the invention, no acid solution is added during the process for the preparation of (S)-glyceraldehyde acetonide from 3,4-O-isopropylidene-L-threonic acid or a salt thereof.

In one embodiment of the invention, the aqueous solution wherein 3,4-O-isopropylidene-L-threonic acid or a salt thereof is present is a buffer system with a pH between 4 and 7. The presence of a buffer system offers a very stable and easy to handle process for the production of (S)-glyceraldehyde acetonide.

Preferably the pH of the buffer system is between 4.5 and 6.5, most preferably between 5 and 6. This buffer may be prepared using various acid/base combinations but preferably a carboxylic acid/carboxylate buffer, for example acetic acid/acetate is used. For instance, in order to maintain the pH value of the aqueous solution between 5 and 6 during the hypochlorite addition, K is possible to use an acetic acid/acetate buffer of approximately pH 5 with a concentration of the acetic acid/acetate chosen such that the pH value after the addition of the full amount of hypochlorite does not exceed 6.

The reaction temperature is in principle not critical. Generally the temperature is taken between 0 and 80° C., but preferably between 15 and 75° C. and most preferably between 25 and 70° C.

The concentration of 3,4-O-isopropylidene-L-threonic acid or a salt thereof in the aqueous solution (before hypochlorite addition) is not critical. Generally this concentration is taken in the range from 0.5 to 30 wt %, preferably in the range from 3 to 25 wt % and most preferably in the range from 7 to 20 wt %.

The total amount—based on the amount of 3,4-O-isopropylidene-L-threonic acid or a salt thereof—of hypochlorite added is generally between 1 and 3 molar equivalents, preferably in an amount of between 1.2 and 2.5 molar equivalents. In order to determine the amount of hypochlorite, the commercial aqueous (alkaline) hypochlorite solution can be assayed for active chlorine by methods known by a person skilled in the art. The molar amount of active chlorine determined is equal to the molar amount of hypochlorite present in the solution.

It has been found that if the aqueous hypochlorite solution is added to the 3,4-O-isopropylidene-L-threonic acid or a salt thereof in aqueous solution in less than 10 minutes, the yield of (S)-glyceraldehyde acetonide is significantly reduced. Therefore, the hypochlorite solution is preferably added in more than 10 minutes, more preferably in more than 20 minutes. For economical reasons (to reduce the amount of reactor capacity), it is preferred not to make the time during which the hypochlorite solution is added too long. In practice therefore, the hypochlorite solution is usually added in less than 2 hours.

(S)-glyceraldehyde acetonide may be extracted from the aqueous solution in a manner known per se, for example as described in example 3 herein. Preferably, (S)-glyceraldehyde acetonide is extracted into tetrahydrofuran.

3,4-O-isopropylidene-L-threonic acid or a salt thereof may be prepared from 5,6-O-isopropylidene-L-ascorbic acid or a salt thereof, by reaction of 5,6-O-isopropylidene-L-ascorbic acid or a salt thereof with hydrogenperoxide ($H_2O_2$) and a base in a manner known per se. Bases which can be used in this process are known to the person skilled in the art and are in principle all bases which can deprotonate hydrogenperoxide under the chosen reaction conditions. Suitable examples of bases include: NaOH, $NaHCO_3$, potassium carbonate, calcium aarbonate and the like. For example, EP-A-0 143 973 shows the production of 3,4-O-isopropylidene-L-threonic acid or a salt thereof by dropwise addition of $H_2O_2$ to a solution of 5,6-O-isopropylidene-L-ascorbic acid and calcium carbonate.

When using calcium carbonate as the base, especially when applied in large scale production, the quality or type of calcium carbonate used may influence the yield of (S)-glyceraldehyde acetonide produced in a subsequent step. Which calcium carbonate is most advantageous can easily be determined by the person skilled in the art by testing calcium carbonate from different suppliers (e.g. from Acros, Merck, Lithos) and by comparing the yields of the (S)-glyceraldehyde acetonide obtained in a subsequent step.

In order to obtain a satisfactory conversion of 5,6-O-isopropylidene-L-ascorbic acid or a salt thereof to 3,4 isopropylidene-L-threonic acid or a salt thereof an excess of $H_2O_2$, based on 5,6-O-isopropylidene-L-ascorbic acid or a salt thereof is usually used. For safety reasons, the remaining $H_2O_2$ is preferably removed prior to further processing, for example by using metal catalysts, which decompose the $H_2O_2$ into $H_2O$ and $O_2$. For instance, in EP-A-143 973, it is shown that in a process for the production of 3,4-O-isopropylidene-L-threonic acid from 5,6-O-isopropylidene-L-ascorbic acid $H_2O_2$ may be decomposed by using palladium-on-arbon (Pd/C). Use of metal catalysts, such as Pd/C, for the removal of excess $H_2O_2$ has several disadvantages.

For example, metal catalysts, such as Pd/C, need to be removed prior to further processing (such as for example the conversion of the formed 3,4-O-isopropylidene-L-threonic acid or a salt thereof to (S)-glyceraldehyde acetonide). Such a removal of the Pd/C-catalyst results in the loss of a significant amount of the 3,4-O-isopropylidene-L-threonic acid or a salt thereof (and hence a lower yield). Additionally, metal catalysts such as Pd/C are expensive and difficult to recycle. Also, the $H_2O_2$ decomposition reaction with metal catalysts usually requires an elevated temperature giving partial loss of the 3,4-O-isopropylidene-L-threonic acid or a salt thereof due to side reactions and leading to a potentially hazardous situation due to the coincidence of a high $O_2$ concentration and a high temperature.

It has been found that these disadvantages are overcome if catalase is used to remove $H_2O_2$. By using catalase, a higher yield is obtained, catalase is cost-effective (since only small amounts of catalase are sufficient to remove excess $H_2O_2$) and the $H_2O_2$ decomposition with catalase can be conducted at ambient temperature so that no 3,4-O-isopropylidene-L-threonic acid or a salt thereof is lost by side reactions and the risk of a potentially hazardous situation is minimized.

Therefore, in a preferred embodiment of the invention, the invention also relates to a process for the preparation of (S)-glyceraldehyde acetonide from 3,4-O-isopropylidene-L-threonic acid or a salt thereof in aqueous solution, and hypochlorite in aqueous solution, wherein during addition of at least 0.1 molar equivalent of hypochlorite based on the amount of 3,4-O-isopropylidene-L-threonic acid or a salt thereof, an acid solution is not simultaneously added and wherein the hypochlorite solution has a pH>7.5, wherein 3,4-O-isopropylidene-L-threonic acid or a salt thereof is prepared from 5,6-O-isopropylidene-L-ascorbic acid or a salt thereof in the presence of $H_2O_2$ and a base in a manner known per se and optionally the excess $H_2O_2$ is removed by catalase.

In the scope of the invention, with catalase is meant an enzyme which is capable of converting $H_2O_2$ into $H_2O$ and $O_2$ and which belongs to the enzyme group EC 1.11.1.6, i.e., enzymes which do not need a donor, such as for example $NADH_2$, palmitate or ferrocytochrome C. Catalase from various sources is commercially available.

Catalase may be added in every form. This includes, for example catalase as a dry powder, in solution, as an immobilized enzyme etc.

The optimal amount of catalase to be added can be determined by a person skilled in the art; the upper boundary of the amount of catalase being determined by foaming problems (due to almost instantaneous formation of the full amount of $O_2$ and the lower boundary being determined by too long reaction times.

5,6-O-isopropylidene-L-ascorbic acid or a salt thereof on its turn may be prepared from L-ascorbic acid or a salt thereof by reacting L-ascorbic acid or a salt thereof with an acetonide forming agent, preferably in the presence of an acid catalyst. In the scope of the invention with acetonide forming agent is meant a reagent which can be used to convert a diol into an acetonide, for example acetone, 2,2-dimethoxy-propane or 2-methoxy-propene. Examples of an acid catalyst include p-toluenesulfonic acid or methanesulfonic acid.

As said before, (S)-glyceraldehyde acetonide is a useful intermediate in the synthesis of, for instance drugs, in particular anti-viral drugs, agrochemicals and the like. WO03/022853 describes for instance a process for the preparation of the following compounds (in particular the preparation of several compounds in enantiomerically enriched form): (2-(2,2-dimethyl-[1,3]dioxolan-4-ylmethylene)-malonic acid diethyl ester; 2-[1-(2,2-dimethyl-[1,3]dioxolanyl)-2-nitroethyl]-malonic acid dimethyl ester; 4-methoxy-2-oxo-hexahydro-furo[3,4-b]furan-3-carboxylic acid methyl ester; 2-(4-hydroxy-2-methoxy-tetrahydro-furan-3-yl)-malonic acid dimethyl ester; 4 methoxy-tetrahydro-furo[3,4-b]furan-2-one, 4-hydroxy-2-methoxy-tetrahydro-furan-3-yl) acetic acid methyl ester; hexahydro-furo[2,3-b]furan-3-ol) starting from (S)-glyceraldehyde acetonide. These compounds can be used, in particular in enantiomerically enriched form, in the preparation of anti-viral drugs, in particular anti-HIV drugs, more in particular HIV protease inhibitors. These compounds will be indicated below using the reference numbers as used in WO03/022853. The compounds are of particular interest in preparing HIV protease inhibitors as disclosed in WO 95/24385, WO99/65870, WO 00/47551, WO 00/76961 and U.S. Pat. No. 6,127,372, WO 01/25240, EP 0 715 618 and WO 99/67417 all incorporated herein by reference, and in particular in preparing the following HIV protease inhibitors:

[(1S,2R)-2-hydroxy-3-[[(4-methoxyphenyl)sulfonyl](2-methylpropyl)amino]-1-(phenylmethyl)propyl]-carbamic acid (3R,3aS,6aR)-hexahydrofuro[2,3-b]furan-3-yl ester (HIV protease inhibitors);

[(1S,2R)-3-[[(4-aminophenyl)sulfonyl](2-methylpropyl) amino]-2-hydroxy-1-(phenylmethyl)propyl]-carbamic acid (3R,3aS,6aR)-hexahydrofuro[2,3-b]furan-3-yl ester (HIV protease inhibitor 2);

[(1S,2R)-3-[(1,3-benzodioxol-5-ylsulfonyl)(2-methylpropyl)amino]-2-hydroxy-1-(phenylmethyl)propyl]-carbamic acid (3R,3aS,6aR)hexahydrofuro[2,3-b]furan-3-yl ester (HIV protease inhibitor 3), or any pharmaceutically acceptable addition salt thereof.

According to WO03/022853, 2-(2,2-dimethyl-[1,3]dioxolan-4-ylmethylene)-malonic acid diethyl ester (compound III.2) can be prepared from (S)-glyceraldehyde acetonide using dimethylmalonate. 2-[1-(2,2-dimethyl-[1,3]dioxolan-4-yl)-2-nitroethyl]-malonic acid dimethyl ester (compound III.3) can be prepared by reaction of 2-(2,2-dimethyl-[1,3] dioxolan-4-ylmethylene)-malonic acid diethyl ester (compound III.2) with nitromethane in the presence of a catalytic amount of 1,8-diazabicyclo[5.4.0]undec-7-ene (DBU). 4-Methoxy-2-oxo-hexahydro-furo[3,4-b]furan-3-carboxylic acid methyl ester (compound III.4) and 2-(4-hydroxy-2-methoxy-tetrahydro-furan-3-yl)-malonic acid dimethyl ester (compound III.4') can be prepared from 2-[1-(2,2-dimethyl-[1,3]dioxolan-4-yl)-2-nitroethyl]-malonic acid dimethyl ester (compound III.3) by using first a base and subsequently an acid. The compounds 4-methoxy-tetrahydro-furo[3,4-b]furan-2-one (compound III.5) and 4-hydroxy-2-methoxy-tetrahydrofuran-3-yl) acetic acid methyl ester (compound III.5°) may be prepared by decarboxylation of the compounds 4-methoxy-2-oxo-hexahydro-furo[3,4-b]furan-3-carboxylic acid methyl ester (compound III.4) and 2-(4-hydroxy-2-methoxy-tetrahydro-furan-3-yl)-malonic acid dimethyl ester (compound III.4'). Hexahydro-furo[2,3-b]furan-3-ol (compound 7.1) can be prepared by reduction of 4-methoxy-tetrahydro-furo[3,4-b]furan-2-one (compound III.5), which results in the intermediate compound: 4-(2-hydroxy-ethyl)-5-methoxy-tetrahydro-furan-3-ol (compound of formula (6)), which can then be cyclisized to form hexahydro-furo[2,3 b]furan-3-ol (compound 7.1.).

The process of the invention will now be elucidated by way of the following examples without however being limited thereto.

EXAMPLES

To illustrate the examples, the scheme below has been added. Please note that this scheme is in no way meant to limit the scope of the invention.

Scheme

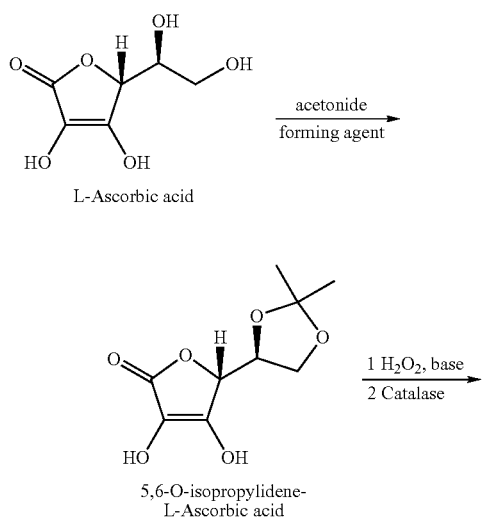

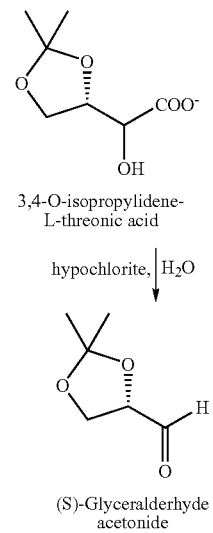

Example 1

Conversion of 5,6-O-isopropylidene-L-ascorbic Acid to 3,4-O-isopropylidene-L-threonic Acid Calcium Salt with Decomposition of Excess $H_2O_2$ with Catalase To a cooled (0° C.) suspension of 725 g (7.25 mole) $CaCO_3$ in 7040 g water, 875 g (4.05 mole) of 5,6-O-isopropylidene-L-ascorbic acid was added portionwise during 1 h. Subsequently, 1 g Perenol AMH-2 anti-foaming agent was added. To the resulting reaction mixture, 1420 g aqueous $H_2O_2$ (30 wt % solution, 12.53 mole) was added dropwise over 3½ h, while the temperature was kept between 0 and 10° C. The reaction mixture was kept at 0° C. overnight and then slowly heated to ambient temperature after which a solution of 1 g catalase (from bovine liver, Roche Diagnostics, 649400 U/ml) in 10 ml water was added dropwise during 1 h. After stirring for 1 h the remaining amount of $H_2O_2$ was <0.5 ppm (as shown by a peroxide test strip, Merck Merckoquant 1.10011.0001) and the reaction mixture was heated to 50° C. and 200 g Decalite™ was added. The reaction mixture was filtered over a Büchner funnel and the solids were subsequently washed with 2.0 L warm (50° C.) water, yielding 10019 g filtrate containing 717.2 g (1.84 mole) of 3,4-O-isopropylidene-L-threonic acid calcium salt with a chemical yield of 91% based on 5,6-O-isopropylidene-L-ascorbic acid. This solution was evaporated in vacuo to a stock solution containing 8.09 wt % 3,4-O-isopropylidene-L-threonic acid calcium salt for further use in examples 2 and 3.

Comparative Example A

Conversion of 5,6-O-isopropylidene-L-ascorbic Acid to 3,4-O-isopropylidene-L-threonic Acid Calcium Salt with Decomposition of Excess $H_2O_2$ with Pd/C To a cooled (0° C.) suspension of 72.5 g $CaCO_3$ (0.725 mole) in 704 g water, 88.3 g (0.409 mole) of 5,6-O-isopropylidene-L-ascorbic acid was added portionwise during 30 min. To the resulting reaction mixture was added 0.12 ml Perenol AHM-2 anti-foaming agent and subsequently 142 g aqueous $H_2O_2$ (30 wt % solution, 1,253 mole) was added dropwise over a period of 2½ h, while maintaining the internal temperature between 0 and 5° C. The reaction mixture was stirred for an additional 2½ h at 0° C., subsequently heated to 20° C. during 2 h, stirred at 20° C. overnight and heated to 50° C. after which 2.0 g Pd/C (20 wt %) and 16 g of activated carbon were added successively. The mixture was stirred for 30 min after which the remaining amount of $H_2O_2$ was <0.5 ppm (as shown by a peroxide test strip, Merck Merckoquant 1.10011.0001). Subsequently, 16 g Decalite™ was added, the mixture stirred for an additional 30 min and filtered over a Büchner funnel and the solids subsequently washed twice with 100 ml warm (50° C.) water yielding 1022 g of filtrate containing 61.7 g (0.158 mole) 3,4-O-isopropylidene-L-threonic acid calcium salt with a chemical yield of 77% based on 5,6-O-isopropylidene-L-ascorbic acid.

In conclusion, the special embodiment of the invention using catalase leads to a higher yield of the 3,4-O-isopropylidene-L-threonic acid calcium salt (example 1) than if a Pd/C catalyst is used (comparative example A).

Example 2

Conversion of 3,4O-isopropylidene-L-threonic Acid Calcium Salt to (S)-glyceraldehyde Acetonide without Addition of Acid Of the aqueous 8.09 wt % 3,4-O-isopropylidene-L-threonic acid calcium salt stock solution as obtained in Example 1 was taken 482 g (containing 39.0 g, 100 mmole 3,4-O-isopropylidene-L-threonic acid calcium salt) which was further concentrated in vacuo to 312 g and subsequently heated to 50° C. To this solution was added dropwise over 41 min 146.4 g of an aqueous sodium hypochlorite solution (Acros, 12.6% weight active $Cl_2$). During the addition the pH initially increased to 6.9 and then rapidly decreased to a stable value of 5.9. The mixture was cooled to ambient temperature (with the pH still being 5.9) and subsequently analysed by GC showing that 18.46 g (S)-glyceraldehyde acetonide had been obtained with a chemical yield of 71% based on 3,4-O-isopropylidene-L-threonic acid calcium salt.

Example 3

Conversion of 3,4-O-isopropylidene-L-threonic Acid Calcium Salt to (S)-glyceraldehyde Acetonide without Addition of Acid, in the Presence of Acetic Acid/Acetate Buffer Of the aqueous 8.09 wt % 3,4-O-isopropylidene-L-threonic acid calcium salt stock solution as obtained in Example 1 was taken 801.3 g (containing 64.8 g, 166.2 mmole 3,4-O-isopropylidene-L-threonic acid calcium salt) which was further concentrated in vacuo to 581.1 g. To this solution were successively added 57.1 g sodium acetate and 21.1 g of glacial acetic acid, yielding an aqueous solution of 3,4-O-isopropylidene-L-threonic acid with a pH value of 5.0. The resulting mixture was heated to 50° C. and 261.6 g of an aqueous sodium hypochlorite solution (Acros, 12.6% weight active $Cl_2$) was added dropwise over 1 h. The reaction mixture was stirred for an additional 55 minutes and subsequently cooled to ambient temperature; the pH had become 6.0. After the addition of 150 g NaCl the mixture was extracted four times with 750 ml tetra hydro furan (THF), yielding 2624 g extract containing 29.4 g (226.2 mmole) (S)-glyceraldehyde acetonide with a chemical yield of 68% based on 3,4-O-isopropylidene-L-threonic acid calcium salt Example 4

Large-scale Production of (S)-glyceraldehyde Acetonide from 5,6-O-isopropylidene L-ascorbic Acid via 3,4-O-isopropylidene L-threonic Acid Calcium Salt, Wherein in the Conversion of 3,4-O-isopropylidene L-threonic Acid Calcium Salt to (S)-glyceraldehyde Acetonide no Acid is Added 340 kg of water and 40.1 kg of calcium carbonate were charged to a 1000 ltr reactor and the resulting mixture was cooled to 0° C. Subsequently, 48.05 kg (222.5 mole) of –5,6-O-isopropylidene L-ascorbic acid was added portionwise during 60 min. After stirring for 15 minutes at 0° C., 66.8 kg of aqueous hydrogen peroxide (35 wt %) was dosed during 5 hours, while maintaining the internal temperature at 0-10° C. The reaction mixture was slowly warmed to 20° C. and subsequently stirred at this temperature for 1 hour. 40 kg of the filter aid Decalite™ was added to the reactor, the mixture was filtered and excess peroxide in the filtrate was destroyed by the addition of catalase giving 536 kg of an aqueous 3,4-O-isopropylidene L-threonic acid calcium salt solution [assay 7.24 wt % 3,4-O-isopropylidene L-threonic acid calcium salt, corresponding to 38.8 kg of 3,4-O-isopropylidene L-threonic acid calcium salt (99.4 mole, yield 89.4% based on 5,6-O-isopropylidene L-ascorbic acid)]. This solution was concentrated to 230 kg by means of a vacuum distillation and the resulting solution was warmed to 50° C. Subsequently, 128.8 kg of hypochlorite (assay 169.3 g/l of active chlorine) was dosed in 1 hour time and the mixture stirred for an additional 30 minutes at this temperature. After cooling to 20° C. 370 kg of (S)-glyceraldehyde acetonide solution was obtained (assay (S)-glyceraldehyde acetonide 4.7 wt %, corresponding to 17.4 kg of (S)-glyceraldehyde acetonide=133.8 mole. Yield=67.2% based on 3,4-O-isopropylidene L-threonic acid calcium salt, Yield=60.1% based on 5,6-O-isopropylidene L-ascorbic acid.

Comparative Example B

Conversion of 3,4-O-isopropylidene-L-threonic Acid Calcium Salt to (S)-glyceraldehyde Acetonide with Simultaneous Addition of Acid To a cooled (0° C.) suspension of 72.1 g $CaCO_3$ (0.72 mole) in 696 g water, 95 g (0.4 mole) of 5,6-O-isopropylidene-L-ascorbic acid was added portionwise during 30 min. Subsequently, 113.3 g aqueous $H_2O_2$ (30 wt % solution, 1.00 mole) was added dropwise over a period of 3½ h, while maintaining the internal temperature at 0° C. The reaction mixture was stirred overnight at 0° C. and subsequently heated to 20° C. during 1 h. 2.0 g Pd/C (20 wt %) and 20 g of activated carbon and 20 g Decalite™ were added successively and the mixture was heated to 50° C. and stirred for 30 min. The reaction mixture was filtered over a Büchner funnel and the solids subsequently washed twice with 100 ml warm (50° C.) water yielding 1005 g of filtrate containing 60.1 g (0.154 mole) 3,4-O-isopropylidene-L-threonic acid calcium salt. This solution was concentrated in vacuo to 523.5 g. Part of this solution (261.7 g) containing 30.1 g (77.2 mmole) 3,4-O-isopropylidene-L-threonic acid calcium salt was heated to 50° C. and subsequently aqueous 4 M HCl solution was added to adjust the pH to 5.0. To this mixture was added dropwise and under vigorous stirring 140.2 g of an aqueous sodium hypochlorite solution (Acros, 12.8% weight active $Cl_2$) during 85 minutes and simultaneously an aqueous 4 M HCl solution was added dropwise (using a pH-stat apparatus) to keep the pH at 5.0. The reaction mixture was subsequently cooled to ambient temperature and analysed by GC showing that 12.3 g (S)-O-glyceraldehyde acetonide had been obtained with a chemical yield of 61% based on 3,4-O-isopropylidene-L-threonic add calcium salt In conclusion, the process of the invention (as shown in examples 2 and 3) leads to a higher yield than the process of comparative example B and does not require difficult reaction control, such as for example the use of a pH-stat.

The invention claimed is:

1. Process for the preparation of (S)-glyceraldehyde acetonide from 3,4-O-isopropylidene-L-threonic acid or a salt thereof in aqueous solution, and hypochlorite in aqueous solution, characterized in that the aqueous hypochlorite solution has a pH>7.5 and in that an acid solution is not simultaneously added during addition of at least 0.1 molar equivalents of the hypochlorite, based on the amount of 3,4-O-isopropylidene-L-threonic acid or a salt thereof.

2. Process according to claim 1, characterized in that an acid solution is not simultaneously added during addition of at least 0.5 molar equivalents of hypochlorite based on the amount of 3,4-O-isopropylidene-L-threonic acid or a salt thereof.

3. Process according to claim 2, characterized in that an acid solution is not simultaneously added during addition of between 1 and 3 molar equivalents of hypochlorite based on the amount of 3,4-O-isopropylidene-L-threonic acid or a salt thereof.

4. Process according to claim 1, characterized in that the aqueous hypochlorite solution has a pH>9.0.

5. Process according to claim 1, characterized in that the aqueous solution of 3,4-O-isopropylidene-L-threonic acid or a salt thereof is a buffer system with a pH between 4 and 7.

6. Process according to claim 5, characterized in that the aqueous solution of 3,4-O-isopropylidene-L-threonic acid or a salt thereof is a buffer system with a pH between 5 and 6.

7. Process according to claim 5, characterized in that the buffer system is formed by an acetic acid/acetate-buffer.

8. Process according to claim 1, characterized in that 3,4-O-isopropylidene-L-threonic acid or a salt thereof is prepared from 5,6-O-isopropylidene-L-ascorbic acid or a salt thereof in the presence of $H_2O_2$ and a base, wherein optionally excess $H_2O_2$ is removed.

9. Process according to claim 8, characterized in that the excess $H_2O_2$ is removed by catalase.

10. Process according to claim 8, characterized in that 3,4-O-isopropylidene-L-threonic acid or a salt thereof is prepared by reaction of L-ascorbic acid or a salt thereof with an acetonide forming agent.

11. Process according to claim 10, characterized in that 3,4-O-isopropylidene-L-threonic acid or a salt thereof is prepared in the presence of an acid catalyst.

12. Process according to claim 1, characterized in that (S)-glyceraldehyde acetonide is extracted from the aqueous solution.

* * * * *